United States Patent [19]

Schaffel

[11] Patent Number: 4,578,349

[45] Date of Patent: Mar. 25, 1986

[54] IMMUNOASSAY FOR CARCINOEMBRYONIC ANTIGEN (CEA)

[75] Inventor: Steven D. Schaffel, Wheeling, Ill.

[73] Assignee: Abbott Laboratories, North Chicago, Ill.

[21] Appl. No.: 366,492

[22] Filed: Apr. 8, 1982

[51] Int. Cl.$^4$ ............... G01N 33/54; G01N 33/56
[52] U.S. Cl. ............................... 435/7; 436/177; 436/813; 436/534; 436/178; 436/179; 436/825
[58] Field of Search .............. 435/7, 810; 436/64, 436/177, 178, 179, 813, 825, 523, 534; 260/112 R

[56] References Cited

U.S. PATENT DOCUMENTS

| | | | |
|---|---|---|---|
| 3,697,638 | 10/1972 | Hansen | 436/825 |
| 4,145,336 | 3/1979 | Edgington et al. | 260/112 R |
| 4,180,556 | 12/1979 | Kim et al. | 436/518 |
| 4,256,724 | 3/1981 | Rutner et al. | 436/531 |
| 4,256,725 | 3/1981 | Rutner et al. | 436/531 |
| 4,272,504 | 6/1981 | Kim et al. | 436/531 |
| 4,299,815 | 11/1981 | Hansen et al. | 435/7 |
| 4,378,344 | 3/1983 | Zahradnik et al. | 435/7 |
| 4,467,031 | 8/1984 | Gallati et al. | 435/7 |

OTHER PUBLICATIONS

Berczi et al., "Detection of Tumor Antibodies in Patients with Gastrointestinal Carcinomas by Solid-Phase Radioimmunoassay", Journal of the National Cancer Institute, 63(3) (1979), pp. 553-566.

Meltzer et al., "Tumor Specific Antigen Solubilized by Hypertonic Potassium Chloride", Journal of the National Cancer Institute 47 (1971), pp. 703-709.

Wu et al., "A Modified Assay for Measuring Human Urinary Carcinoembryonic Antigenic Activity", Biochem Med. 14(3) (1975), pp. 305-316, Abstract only.

Primary Examiner—Thomas G. Wiseman
Assistant Examiner—John E. Tarcza
Attorney, Agent, or Firm—Martin L. Katz; Margaret M. O'Brien

[57] ABSTRACT

This invention involves an improvement in immunoassay for carcinoembryonic antigen in biological fluids. The improvement comprises liberating carcinoembryonic antigen in the biological fluid by diluting the biological fluid with about 0.4–0.8 molar salt solution buffered at about pH 6–8 prior to conducting the immunoassay for carcinoembryonic antigen.

3 Claims, No Drawings

IMMUNOASSAY FOR CARCINOEMBRYONIC ANTIGEN (CEA)

BACKGROUND OF THE INVENTION

Carcinoembryonic antigen (CEA), first described in 1965 by Gold and Freedman, Journal of Experimental Medicine, 121:439, is a tumor-associated antigen. CEA was characterized as a glycoprotein of approximately 200,000 molecular weight with a $\beta$-electrophoretic mobility. (J. Wilson Krupey, et al, Journal of Experimental Medicine, 128:387, 1968 and J. Wilson Krupey, et al, Immunochemistry, 9:617, 1972.) Subsequent development of a radioimmunoassay (RIA) by Thomson, et al (D.M.P. Thomson, et al, Proc. Natl. Acad. Sci., U.S.A., 64:16, 1969) made it possible to detect the very low concentrations of CEA in circulating blood, other body fluids and also in normal and diseased tissues (N. Samcheck, Internal Medicine, 19:413, 1974; V. L. W. Go, et al, Cancer, 36:2346, 1975; and S. K. Khoo, et al, Int. J. Cancer, 11:681, 1973.) Two years later, Hansen, et al, (H. J. Hansen, et al, Clinical Research, 19:143, 1971) developed a modified RIA for CEA.

The results of clinical studies to date indicate that CEA, although originally thought to be specific for digestive tract cancers, is also elevated in other malignancies and in some nonmalignant disorders. (A. M. Steward, et al, Cancer, 33:1246, 1974; P. Oehr, et al, Tumor Diagnostik, 1:40, 1980; and G. Reynoso, et al, Journal of American Medical Association, 220:361, 1972.)

The experience with testing using other methods for assaying CEA has shown that CEA testing can have significant value in the monitoring of patients with diagnosed malignancies during treatment. A persistent elevation in circulating CEA following treatment is strongly indicative of occult metastatic and/or residual disease. (N. Zamcheck, Symposium of Clinical Application of CEA and Other Antigenic Markers Assays, Nice, France, October, 1977, Amsterdam, Oxford, Medica Exerpta, 1978; and E. W. Martin, et al, American Journal of Surgery, 137:167, 1979.) A persistently rising CEA value may be associated with progressive malignant disease and poor therapeutic response. (A. T. Sharin, et al, Cancer, 33:1239, 1974.) A declining CEA value is generally indicative of a favorable prognosis and good response to treatment. (J. J. Lokich, et al, Annals of Internal Medicine, 89:902, 1978.)

Patients who have low pretherapy CEA levels may later show elevations in CEA level as an indication of progressive disease.

Clinical relevance of the CEA assay is best known in the follow-up management of patients with colorectal carcinoma, but value has been shown also for serial monitoring of CEA levels in patients with adenocarcinoma arising in other digestive system organs, as well as in the lungs, breast and prostate, and in patients with epidermoid carcinomas of the lung, esophagus and genitourinary system.

The CEA level also provides prognostic information. Long-term follow-up studies of pateints with colorectal and resectable lung carcinoma suggest that the preoperative CEA level has prognostic significance. (H. S. Wanebo, et al, New England Journal of Medicine, 299:448, 1978 and J. P. Concannon, et al, Cancer, 42:1477, 1978.)

More recently a solid phase enzyme immunoassay based on the "sandwich" principle has been developed and commercially sold by Abbott Laboratories, North Chicago, Ill., all under the tradename CEA-EIA or CEA-RIA. Beads coated with guinea pig anti-CEA are incubated with heat-treated specimen supernatants and the appropriate standards and controls. During this incubation, CEA present in the specimen is bound to the beads. Nonreactive components are removed by aspiration of fluid and washing of the beads. Goat anti-CEA conjugated with horseradish peroxidase or $I^{125}$ is incubated with the beads and, if CEA were present in the specimen, the anti-CEA:horseradish peroxidase conjugate or anti-CEA $I^{125}$ conjugate is bound to the CEA on the beads. Unbound conjugate is removed by aspiration and the beads washed. The beads are next incubated with enzyme substrate solution (hydrogen peroxide and orthophenylenediamine.2HCl) to develop a color which is a measure of the amount of bound anti-CEA:-horseradish peroxidase conjugate. The enzyme reaction is stopped by the action of N hydrochloric acid and the intensity of color developed is read using the spectrophotometer set at 492 nm. The intensity of the color formed by the enzyme reaction is proportional to the concentration of CEA in the specimen within the working range of the assay. For the CEA-RIA assay the amount of $I^{125}$ conjugate bound to the beads is determined by counting in a gamma scintillation counter. A standard curve is obtained by plotting the CEA concentration of the standards vs. the absorbance (or counts per minute). The CEA concentration of the unknowns and controls run concurrently with the standards can be determined from the cruve.

Problems with CEA assays have generally involved pretreatment and extraction techniques to liberate CEA in a biological fluid such as serum or plasma. Various heat treatment and perchloric acid extractions have been used. This invention avoids the need for elaborate pretreatment and simplifies immunoassays for CEA.

SUMMARY OF THE INVENTION

This invention involves an improvement in immunoassays for CEA which eliminates laborious pretreatment steps. The improvement comprises liberating CEA by diluting the biological fluid to be tested for CEA with a 0.4–0.8 molar salt solution buffered at pH 6–8 prior to conducting the immunoassay.

DETAILED DESCRIPTION OF THE INVENTION

This invention involves diluting biological fluids such as serum, plasma, and intestinal fluid with a diluent which is a 0.4–0.8 molar salt solution buffered at pH 6–8. Thereafter, immunoassays are conducted by art recognized techniques. Thus, 0.4–0.8, preferably 0.5, molar sodium chloride, potassium chloride, magnesium chloride and salts with like properties are suitable diluents. These salt solutions are buffered at pH 6–8 with common buffers such as 0.1 molar Tris-hydroxymethyl aminomethane and 0.01 molar sodium phosphate. 0.1–0.2 Molar sodium chloride solution is not effective in liberating CEA in biological fluids.

DESCRIPTION OF THE PREFERRED EMBODIMENT

I. Specimen Dilution Buffer Composition 1. 0.1 M tris-hydroxymethyl-aminomethane (Tris) pH 7.0 to 8.0 containing 0.5 M sodium chloride (NaCl) (alternatively can contain potassium chloride or magnesium chloride and similar salts at the same concentration) and 0.1% bovine serum albumin (BSA).

2. Alternate buffer is 0.01 M sodium phosphate pH 7.0 to 8.0 containing the same salts and BSA at the concentrations noted in 1.

II. Assay Procedure

1. Adjust temperature of water bath to 45°±1° C.
2. Identify reaction tray wells with data sheet for testing the standards and specimens.
3. Using precision pipettes, add 0.2 ml of standards to their assigned wells.
4. Using precision pipettes, add 0.1 ml of specimen to their assigned wells.
5. Add 0.1 ml of specimen dilution buffer to each well containing a specimen.
6. Using forceps, dispense one anti-CEA coated bead into each well containing a test specimen.
7. Apply cover sealer to each tray. Gently tap trays to ensure that each bead is covered with the sample and that any air bubbles are released.
8. Incubate the trays in the 45°±1° C. water bath for two hours (±5 mintues).
9. At the end of the two-hour incubation period, remove the trays from the water bath. Remove and discard the cover sealers. Aspirate the liquid and wash each well and bead two times with 4 to 5 ml of distilled or deionized water for a total rinse volume of 8 to 10 ml.
10. Add 0.2 ml of anti-carcinoembryonic antigen (goat): peroxidase (horseradish) conjugate to each well containing a bead.
11. Apply cover sealer to each tray. Make sure that beads are completely covered with liquid by tapping the trays to release any air bubbles that may be trapped in the solution.
12. Incubate the trays for two hours (±5 minutes) in the 45°±1° C. water bath.
13. At the end of the two-hour incubation, remove the trays from the water bath. Remove and discard the cover sealers. Aspirate the liquid and wash each well and bead two times with 4 to 5 ml of distilled or deionized water for a total rinse volume of 8 to 10 ml. Remove all excess liquid from tray by aspiration or blotting.
14. Immediately transfer beads from wells to properly identify assay tubes. Align inverted rack of oriented tubes over the tray, press tubes tightly over wells, then invert tray and tubes together so that beads fall into corresponding tubes.
15. Pipette 0.3 ml of the freshly prepared orthophenylenediamine.2HCl substrate solution into each tube containing a bead.

NOTE: Substrate solution should be clear to pale yellow. Do not allow substrate to come into contact with any metal. The orthophenylenediamine.2HCl is prepared by dissolving a tablet containing 27 mg of citrate phosphate buffer pH 5.5.

16. Incubate tubes at room temperature (15° to 30° C.) for 30 minutes±1 minute. To prevent foreign material from contaminating the mixture and excessive light from affecting color development, cover the box until incubation is complete.

17. Stop the enzyme reaction by adding 2.0 ml of 1 N hydrochloric acid to each tube at 30 minutes±1 minute after the addition of orthophenylenediamine.2HCl substrate solution to that tube. Mix (vortex or equivalent) each tube thoroughly.

NOTE: Do not allow acid solution to come in contact with metal. Air bubbles should be removed prior to reading absorbance. All absorbances should be determined within two hours after addition of 1 N hydrochloric acid.

18. Set Quantum I, spectrophotometer sold by Abbott Laboratories, North Chicago, Ill. in mode 2 and blank using a reaction tube containing distilled or deionized water. Read CEA standards, positive control and unknowns.

If the Quantum I spectrophotometer is not used, set the photometer or spectrophotometer at 492 nm and zero the instrument using distilled or deionized water. Determine the absorbance of the standards, controls and unknowns. Be sure that the cuvette is free of color residue from previous specimens.

19. If, in an initial assay, a specimen is found to contain greater than 60 ng CEA/ml. dilute the specimen with an appropriate amount of the specimen dilution buffer. For example, a ten-fold dilution can be made by adding 0.1 ml of the specimen to 0.9 ml of the specimen dilution buffer. Mix thoroughly before assaying.

In a radioimmunoassay, the enzyme labeled CEA antibody is replaced by $I^{125}$ labeled antibody and the number of counts on the bead are determined by a gamma scintillation counter.

What is claimed is:

1. In an immunoassay for carcinoembryonic antigen in biological fluid, which immunoassay comprises the steps of contacting the biological fluid with antibody to carbinoembryonic antigen and determining the extent of antibody binding to the carcinoembryonic antigen, the improvement comprising liberating carcinoembryonic antigen in the biological fluid by diluting the biological fluid with a diluent comprising a 0.4–0.8 molar salt solution buffered at a pH within the range of from 6 to 8, prior to conducting the immunoassay for carcinoembryonic antigen.

2. The immunoassay for carcinoembryonic antigen according to claim 1 wherein the immunoassay for carcinoembryonic antigen is an enzyme or radioimmunoassay.

3. The immunoassay for carcinoembryonic antigen according to claim 2 wherein the immunoassay for carcinoembryonic antigen is an enzyme or radioimmunoassay wherein the biological fluid is contacted with a bead coated with antibody to carcinoembryonic antigen, the bead is washed, contacted with enzyme or $I^{125}$ labeled antibody carcinoembryonic antigen, washed and the enzyme or $I^{125}$ on the bead is measured.

* * * * *

UNITED STATES PATENT AND TRADEMARK OFFICE
CERTIFICATE OF CORRECTION

PATENT NO. : 4,578,349
DATED : March 25, 1986
INVENTOR(S) : S. Schaffel

It is certified that error appears in the above—identified patent and that said Letters Patent is hereby corrected as shown below:

IN THE CLAIMS

Claim 1, line 4, delete "carbinoembryonic" and insert

- carcinoembryonic -.

Signed and Sealed this

Twenty-third Day of September 1986

[SEAL]

Attest:

DONALD J. QUIGG

Attesting Officer

Commissioner of Patents and Trademarks